(12) United States Patent
Fukuchi et al.

(10) Patent No.: US 11,220,471 B2
(45) Date of Patent: Jan. 11, 2022

(54) METHOD FOR PRODUCING TETRAFLUOROMETHANE

(71) Applicant: SHOWA DENKO K.K., Tokyo (JP)

(72) Inventors: Yohsuke Fukuchi, Tokyo (JP); Tomokazu Sugawara, Tokyo (JP); Shinya Oguro, Tokyo (JP); Hiroshi Kobayashi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/962,943

(22) PCT Filed: Dec. 25, 2018

(86) PCT No.: PCT/JP2018/047654
§ 371 (c)(1),
(2) Date: Jul. 17, 2020

(87) PCT Pub. No.: WO2019/142627
PCT Pub. Date: Jul. 25, 2019

(65) Prior Publication Data
US 2021/0363078 A1 Nov. 25, 2021

(30) Foreign Application Priority Data
Jan. 19, 2018 (JP) ............................. JP2018-007189

(51) Int. Cl.
*C07C 17/367* (2006.01)
*C07C 17/20* (2006.01)
(Continued)

(52) U.S. Cl.
CPC .......... *C07C 17/367* (2013.01); *C07C 17/204* (2013.01); *C07C 17/361* (2013.01); *C07C 19/08* (2013.01)

(58) Field of Classification Search
CPC ..... C07C 17/367; C07C 17/361; C07C 19/08; C07C 17/204
See application file for complete search history.

(56) References Cited

U.S. PATENT DOCUMENTS

| 4,158,023 A | 6/1979 | von Halasz |
| 7,064,240 B2 * | 6/2006 | Ohno ................. C23G 5/02803 570/161 |

(Continued)

FOREIGN PATENT DOCUMENTS

| CN | 102140054 A | 8/2011 |
| JP | 53-119802 A | 10/1978 |

(Continued)

OTHER PUBLICATIONS

International Search Report for PCT/JP2018/047654, dated Mar. 19, 2019.

(Continued)

*Primary Examiner* — Jafar F Parsa
(74) *Attorney, Agent, or Firm* — Sughrue Mion, PLLC

(57) ABSTRACT

Provided is a method for producing tetrafluoromethane, and the method is unlikely to damage a reaction apparatus and can produce tetrafluoromethane safely, inexpensively, and stably. To a raw material liquid (1) containing a reaction inducer and a fluorinated hydrocarbon represented by chemical formula $C_pH_qCl_rF_s$ (in the chemical formula, p is an integer of 3 or more and 18 or less, q is an integer of 0 or more and 3 or less, r is an integer of 0 or more and 9 or less, and s is an integer of 5 or more and 30 or less) and having no carbon-carbon unsaturated bond, fluorine gas is introduced to give tetrafluoromethane. The reaction inducer is a hydrocarbon polymer solid at normal temperature and (Continued)

pressure and is reacted with fluorine gas to induce a reaction of forming tetrafluoromethane from the fluorinated hydrocarbon and the fluorine gas.

6 Claims, 1 Drawing Sheet

(51) Int. Cl.
  *C07C 17/361* (2006.01)
  *C07C 19/08* (2006.01)

(56) References Cited

U.S. PATENT DOCUMENTS

2003/0157800 A1  8/2003  Ohno et al.
2014/0332078 A1  11/2014  Guo et al.

FOREIGN PATENT DOCUMENTS

| | | |
|---|---|---|
| JP | 59-13739 A | 1/1984 |
| JP | 01-180838 A | 7/1989 |
| JP | 01-180839 A | 7/1989 |
| JP | 06-298681 A | 10/1994 |
| JP | 11-180706 A | 7/1999 |
| JP | 2002-069014 A | 3/2002 |
| TW | I485154 B | 5/2015 |

OTHER PUBLICATIONS

International Preliminary Report on Patentability dated Jul. 30, 2020, with translation of Written Opinion in International Application No. PCT/JP2018/047654.

* cited by examiner

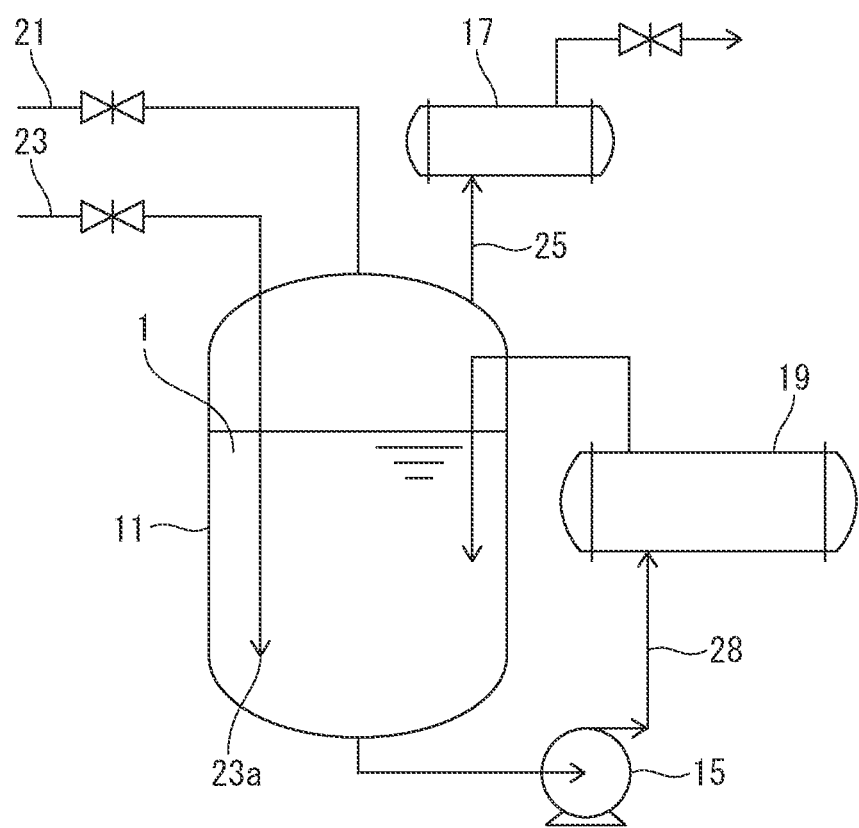

METHOD FOR PRODUCING TETRAFLUOROMETHANE

CROSS REFERENCE TO RELATED APPLICATIONS

This application is a National Stage International of Application No. PCT/JP2018/047654 filed Dec. 25, 2018, claiming priority based on Japanese Patent Application No. 2018-007189 filed Jan. 19, 2018.

TECHNICAL FIELD

The present invention relates to a method for producing tetrafluoromethane.

BACKGROUND ART

Known methods for producing tetrafluoromethane include a method of reacting solid carbon with fluorine gas, a method of reacting a gaseous hydrocarbon with fluorine gas, and a method of reacting a mixture of a carbon material and a metal, a metal fluoride, or a fused alumina with fluorine gas (see PLTs 1 and 2).

The method of reacting solid carbon with fluorine gas is a combustion reaction with flames and generates a great amount of reaction heat, and thus the material itself of an outlet of fluorine gas or a reaction container may be reacted with fluorine gas to corrode. A reaction without flames may generate insufficient reaction heat, giving tetrafluoromethane at a lower yield.

The method of reacting a gaseous hydrocarbon with fluorine gas is also a combustion reaction with flames and generates a great amount of reaction heat, and thus the material itself of an outlet of fluorine gas or a reaction container may be reacted with fluorine gas to corrode. For a reaction without flames, fluorine gas is diluted with an inert gas such as nitrogen gas to suppress the reaction heat, but such a measure needs a step of separating and purifying the resulting tetrafluoroethane from an inert gas, and this increases the production cost unfortunately.

The method of reacting a mixture of a carbon material and a metal, a metal fluoride, or a fused alumina with fluorine gas is a method of mildly reacting a carbon material with fluorine gas, is not performed in such a reaction condition as to cut carbon-carbon bonds, and is unsuitable for the synthesis of tetrafluoromethane.

CITATION LIST

Patent Literature

PTL 1: JP 6-298681 A
PTL 2: JP 11-180706 A

SUMMARY OF INVENTION

Technical Problem

As described above, in conventional methods for producing tetrafluoromethane, such a vigorous reaction as to damage a reaction apparatus is performed, whereas a reaction in a mild condition suppresses damages on a reaction apparatus but is unlikely to give tetrafluoromethane as a main product.

The present invention is intended to provide a method that is for producing tetrafluoromethane, is unlikely to damage a reaction apparatus, and can produce tetrafluoromethane safely, inexpensively, and stably.

Solution to Problem

To solve the problems, aspects of the present invention are the following [1] to [4].

[1] A method for producing tetrafluoromethane, the method including
introducing fluorine gas to a raw material liquid containing a reaction inducer and a fluorinated hydrocarbon represented by chemical formula $C_pH_qCl_rF_s$ (in the chemical formula, p is an integer of 3 or more and 18 or less, q is an integer of 0 or more and 3 or less, r is an integer of 0 or more and 9 or less, and s is an integer of 5 or more and 30 or less) and having no carbon-carbon unsaturated bond,
in which the reaction inducer is a hydrocarbon polymer solid at normal temperature and pressure and is reacted with the fluorine gas to induce a reaction of forming tetrafluoromethane from the fluorinated hydrocarbon and the fluorine gas.

[2] The method for producing tetrafluoromethane according to the aspect [1], in which the reaction inducer is contained at a content of more than 0% by mass and not more than 1% by mass where the total content of the fluorinated hydrocarbon and the reaction inducer contained in the raw material liquid is 100% by mass.

[3] The method for producing tetrafluoromethane according to the aspect [2], in which the hydrocarbon polymer is at least one polymer selected from polyethylene, polypropylene, polystyrene, and paraffin.

[4] The method for producing tetrafluoromethane according to any one of the aspects [1] to [3], in which the fluorinated hydrocarbon is at least one fluorine-containing substance selected from a perfluorocarbon, a fluorohydrocarbon, a chlorofluorocarbon, a chlorofluorohydrocarbon, a chlorotrifluoroethylene polymer, and a perfluoropolyether.

Advantageous Effects of Invention

A method according to the present invention enables safe, inexpensive, and stable production of tetrafluoromethane while being unlikely to damage a reaction apparatus.

BRIEF DESCRIPTION OF DRAWINGS

FIG. 1 illustrates an embodiment of a method for producing tetrafluoromethane pertaining to the present invention and is a schematic view illustrating a structure of a reaction apparatus for tetrafluoromethane.

DESCRIPTION OF EMBODIMENTS

An embodiment of the present invention will now be described. The present embodiment is merely an example of the present invention, and the present invention is not limited to the present embodiment. Various modifications or improvements can be made in the present embodiment, and such various modifications and improvements can be encompassed by the present invention.

In a conventional tetrafluoromethane production method of reacting activated carbon with fluorine gas to give tetrafluoromethane, routes through which reaction heat is removed from a reaction field include a route through which heat is discharged outside via a gas heated by reaction heat in an atmosphere and a route through which heat is discharged outside via a reaction apparatus heated by reaction heat (for example, an outlet of fluorine gas or a reaction container). A gas, which unfortunately has a small heat capacity, discharges a small amount of heat, and most of the reaction heat is consumed in heating a reaction apparatus. As a result, a reaction apparatus has a high temperature, thus the reaction apparatus is reacted with fluorine gas, and the reaction apparatus is corroded and damaged.

The inventors of the present invention have carried out intensive studies and consequently have found that by performing a reaction of forming tetrafluoromethane from a fluorinated hydrocarbon and fluorine gas in a liquid phase to reduce the temperature of a reaction field and by further using, in the reaction field, a reaction inducer that induces the reaction of forming tetrafluoromethane from a fluorinated hydrocarbon and fluorine gas, a cleavage reaction of carbon-carbon bonds of a fluorinated hydrocarbon, which is caused only at an extremely high temperature, can be caused in a liquid phase at a low temperature.

In other words, the inventors of the present invention have found that a fluorinated hydrocarbon is difficult to react with fluorine gas even when fluorine gas is blown into a liquid fluorinated hydrocarbon, but when a reaction inducer is used together, the reaction inducer is reacted with fluorine gas, and this reaction induces the reaction between a fluorinated hydrocarbon and fluorine gas at a low temperature to give tetrafluoromethane.

The mechanism is thought as follows: When fluorine gas is blown through an outlet into a liquid fluorinated hydrocarbon, bubbles of the fluorine gas are formed on the periphery of the outlet, and the fluorine gas in the bubbles is reacted with a reaction inducer around the bubbles before the bubbles leave the outlet. By the reaction heat of the reaction, the peripheral fluorinated hydrocarbon vaporizes to react with the fluorine gas in the bubbles. Accordingly, a region having a temperature higher than the temperature of the liquid phase by about 20° C. or more is formed around the outlet (hereinafter called "high temperature reaction region"). When the supply of fluorine gas is continued, the reaction between a fluorinated hydrocarbon and fluorine gas continues in the high temperature reaction region. The resulting reaction heat continuously volatilizes the peripheral liquid phase (i.e., the fluorinated hydrocarbon), and thus the temperature increase of the liquid phase is supposed to be suppressed.

A method for producing tetrafluoromethane pertaining to the present embodiment includes introducing fluorine gas to a raw material liquid containing a reaction inducer and a fluorinated hydrocarbon represented by chemical formula $C_pH_qCl_rF_s$ and having no carbon-carbon unsaturated bond (in the present description, also simply called "fluorinated hydrocarbon"). The reaction inducer is a hydrocarbon polymer solid at normal temperature and pressure and is reacted with fluorine gas to induce a reaction of forming tetrafluoromethane from the fluorinated hydrocarbon and the fluorine gas. In the chemical formula, p is an integer of 3 or more and 18 or less, q is an integer of 0 or more and 3 or less, r is an integer of 0 or more and 9 or less, and s is an integer of 5 or more and 30 or less.

Even when a fluorinated hydrocarbon is difficult to react with fluorine gas, the above mechanism allows the reaction between a reaction inducer and fluorine gas to induce the reaction between a fluorinated hydrocarbon and fluorine gas even at a low temperature. Hence, the temperature is unlikely to abnormally increase in a reaction field, fluorine gas is unlikely to damage a reaction apparatus, and tetrafluoromethane can be safely, inexpensively, and stably produced at a high yield.

In addition, the reaction apparatus is not required to be made from an expensive material having corrosion resistance against fluorine gas (for example, a nickel alloy, Hastelloy (registered trademark), or Monel (registered trademark)), and a reaction apparatus can be made from a general steel such as stainless steel, giving an inexpensive reaction apparatus.

The resulting tetrafluoromethane is useful, for example, as an etching agent for substrates and a cleaning agent for chambers in the semiconductor production process.

Hereinafter, the method for producing tetrafluoromethane pertaining to the present embodiment will be described in further detail.

(1) Fluorinated Hydrocarbon

The fluorinated hydrocarbon is a saturated hydrocarbon represented by chemical formula $C_pH_qCl_rF_s$ and having no carbon-carbon unsaturated bond. The fluorinated hydrocarbon may be any of a linear hydrocarbon, a branched hydrocarbon, and a cyclic hydrocarbon and may be a compound containing no hydrogen atom or no chlorine atom. Examples of the fluorinated hydrocarbon include at least one fluorine-containing substance selected from a perfluorocarbon, a fluorohydrocarbon, a chlorofluorocarbon, a chlorofluorohydrocarbon, a chlorotrifluoroethylene polymer, and a perfluoropolyether.

Specific examples of the chlorotrifluoroethylene polymer include difreon oil (registered trademark), and specific example of the perfluoropolyether include Fomblin oil (registered trademark). The difreon oil is a polychlorotrifluoroethylene having flowability at normal temperature (a pour point of 5 to 15° C.) and having a molecular weight of about 1,000 or less.

The fluorinated hydrocarbon may be any of a gas, a liquid, and a solid at normal temperature and pressure but is preferably a liquid. In the present invention, the normal temperature means 25° C., and the normal pressure means 101.325 kPa (1 atm).

When a fluorinated hydrocarbon is a liquid, the fluorinated hydrocarbon can be mixed with a reaction inducer that is solid at normal temperature and pressure, giving a raw material liquid. The reaction inducer may be dissolved in a liquid fluorinated hydrocarbon or may be dispersed in a powder form. Alternatively, an aggregated reaction inducer may be contained in a liquid fluorinated hydrocarbon.

When a fluorinated hydrocarbon is a liquid, a solvent may be used for the reaction, and the solvent may be mixed with the fluorinated hydrocarbon and a reaction inducer, giving a raw material liquid. In this case, the reaction inducer may be dissolved in a raw material liquid or may be dispersed in a powder form. Alternatively, an aggregated reaction inducer may be contained in a raw material liquid.

When a fluorinated hydrocarbon is a gas or a solid, a solvent is required to be used in the reaction, and the solvent is required to be mixed with the fluorinated hydrocarbon and a reaction inducer to give a raw material liquid. In this case, the reaction inducer may be dissolved in a raw material liquid or may be dispersed in a powder form. Alternatively, an aggregated reaction inducer may be contained in a raw material liquid.

Similarly, a solid fluorinated hydrocarbon may be dissolved in a raw material liquid or may be dispersed in a powder form. Alternatively, an aggregated, fluorinated hydrocarbon may be contained in a raw material liquid. A gaseous fluorinated hydrocarbon may be dissolved in a raw material liquid or may be dispersed as a foam.

As described above, in the method for producing tetrafluoromethane pertaining to the present embodiment, the synthesis reaction of tetrafluoromethane can be performed without solvent or can be performed in a solvent depending on properties of a fluorinated hydrocarbon.

The above fluorinated hydrocarbon is an organic compound that is difficult to react with fluorine gas even when 100% by volume fluorine gas is blown at 40° C. and 101.325 kPa. The reaction formula of a fluorinated hydrocarbon with fluorine gas is represented by the following formula.

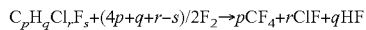

$$C_pH_qCl_rF_s + (4p+q+r-s)/2 F_2 \rightarrow pCF_4 + rClF + qHF$$

In consideration of the reaction formula, to efficiently use the supplied fluorine gas to form tetrafluoromethane, q and r in the chemical formula $C_pH_qCl_rF_s$ are preferably small values.

When p in the chemical formula $C_pH_qCl_rF_s$ is 3 or more, a fluorinated hydrocarbon is not a gas at normal temperature and pressure in many cases (a liquid or a solid in many cases), thus is not required to be cooled or pressurized to make a gas into a liquid, and is economical. When p is 18 or less, a fluorinated hydrocarbon is not a solid at normal temperature and pressure in many cases (a gas or a liquid in many cases), thus is not required to be warmed to make a solid into a liquid, and is economical. p is an integer of 3 or more and 18 or less, preferably an integer of 3 or more and 10 or less, more preferably an integer of 3 or more and 5 or less, and is economically as small as possible because a smaller amount of fluorine gas is needed for production of 1 mol of tetrafluoromethane.

When q in the chemical formula $C_pH_qCl_rF_s$ is 3 or less, a hydrogen atom is reacted with fluorine gas to form hydrogen fluoride as a by-product at a smaller rate, and such a condition is economical because a smaller amount of fluorine gas is needed for production of 1 mol of tetrafluoromethane. q is an integer of 0 or more and 3 or less, preferably an integer of 0 or more and 2 or less, and more preferably 0 or 1. To increase the reaction selectivity of tetrafluoromethane, the fluorinated hydrocarbon is more preferably a perfluorocarbon or a chlorofluorocarbon where q is 0.

When r in the chemical formula $C_pH_qCl_rF_s$ is 0 or more and 9 or less, a fluorinated hydrocarbon is not a solid at normal temperature and pressure in many cases (a gas or a liquid in many cases), thus is not required to be warmed to make a solid into a liquid, and is economical. In addition, a chlorine atom is reacted with fluorine gas to form fluorine chloride as a by-product at a smaller rate, and such a condition is economical because a smaller amount of fluorine gas is needed for production of 1 mol of tetrafluoromethane. r is an integer of 0 or more and 9 or less and preferably an integer of 0 or more and 4 or less. Moreover, the fluorinated hydrocarbon is more preferably a perfluorocarbon where q and r are 0.

(2) Reaction Inducer

The reaction inducer is an organic compound easily reacted with fluorine gas. The reaction inducer is reacted with fluorine gas to induce the reaction of forming tetrafluoromethane from a fluorinated hydrocarbon and fluorine gas and is a hydrocarbon polymer solid at normal temperature and pressure.

Specific examples of the hydrocarbon polymer include at least one polymer selected from polyethylene, polypropylene, polystyrene, and paraffin. The reaction inducer can be reacted with fluorine gas to form tetrafluoromethane in some cases.

As described above, the reaction inducer may be dissolved in a raw material liquid or may be dispersed in a powder form. Alternatively, an aggregated reaction inducer may be contained in a raw material liquid. For example, an aggregated reaction inducer may be attached to an outlet of fluorine gas.

The reaction inducer may be used in any amount as long as the reaction of forming tetrafluoromethane from a fluorinated hydrocarbon and fluorine gas can be induced, and the content of the reaction inducer is preferably more than 0% by mass and not more than 1% by mass and more preferably 0.2% by mass or more and 0.7% by mass or less where the total content of the fluorinated hydrocarbon and the reaction inducer contained in the raw material liquid is 100% by mass. If the reaction inducer is contained at a content of more than 1% by mass, the reaction inducer can function, but hydrogen fluoride may be formed in a larger amount as a by-product, and thus such a condition is uneconomical.

(3) Reaction Apparatus

An example of a reaction apparatus in which the method for producing tetrafluoromethane pertaining to the present embodiment is performed to give tetrafluoromethane will be described with reference to FIG. 1.

A reaction apparatus in FIG. 1 includes a metal reaction container 11 in which a reaction for forming tetrafluoromethane is performed, a raw material liquid introduction pipe 21 through which a raw material liquid 1 containing a fluorinated hydrocarbon represented by chemical formula $C_pH_qCl_rF_s$ and having no carbon-carbon unsaturated bond and a reaction inducer that is a hydrocarbon polymer solid at normal temperature and pressure is introduced to the reaction container 11, a fluorine gas pipe 23 having, at an end, an outlet 23a through which fluorine gas is introduced to a raw material liquid 1 in the reaction container 11, and a gas discharge pipe 25 through which a gas phase in the reaction container 11 is discharged outside. Examples of the metal forming the reaction container 11 include stainless steel. The reaction inducer may be attached to the outlet 23a, and in such a case, from the raw material liquid introduction pipe 21, only a fluorinated hydrocarbon can be introduced.

The reaction apparatus illustrated in FIG. 1 further includes a circulator that extracts a portion of a raw material liquid 1 in the reaction container 11 during reaction outside the reaction container 11 and returns the solution into the reaction container 11. In particular, the respective ends of a circular circulation pipe 28 are connected to the reaction container 11, and a liquid circulating pump 15 installed on the circulation pipe 28 sends a raw material liquid 1. The raw material liquid 1 extracted from the reaction container 11 can be returned through the circulation pipe 28 into the reaction container 11.

A heat exchanger 19 is installed at a point midway of the circulation pipe 28 and at a downstream side of the liquid circulating pump 15 and can cool the extracted raw material liquid 1. The raw material liquid 1 cooled by the heat exchanger 19 is returned into the reaction container 11. In other words, the reaction apparatus illustrated in FIG. 1 is configured to perform reaction while a portion of a raw material liquid 1 in the reaction container 11 is extracted and cooled and the cooled raw material liquid 1 is returned to the reaction container 11.

A produced gas containing tetrafluoromethane formed by reaction can be discharged through the gas discharge pipe 25 outside the reaction container 11. At a downstream side of the gas discharge pipe 25, a heat exchanger 17 is installed and can cool a produced gas discharged from the reaction container 11. Even when a fluorinated hydrocarbon as a raw material vaporizes and is contained in a produced gas, the fluorinated hydrocarbon can be liquified by cooling the produced gas with the heat exchanger 17 and can be returned to the reaction container 11. Hence, an unreacted fluorinated hydrocarbon can be prevented from escaping from the reaction container 11 to the outside and from being lost.

The outlet 23a of the fluorine gas pipe 23 may have any shape, and the outlet 23a can be a round through-hole formed on the fluorine gas pipe 23. The through-hole can have a diameter of, for example, 0.5 mm or more and 5 mm or less. The fluorine gas pipe 23 may have one or a plurality of outlets 23a. To an end or the vicinity of the outlet 23a, an aggregated reaction inducer may be attached. Near the outlet 23a, a temperature measurement device such as a thermocouple may be installed to measure the temperature near the outlet 23a.

Near the outlet 23a of fluorine gas, a high temperature reaction region is formed as described above, and it is preferable that the high temperature reaction region be not in contact with a member of the reaction apparatus, such as a chamber wall of the reaction container 11, a thermocouple, a stirring blade, and a baffle plate. A portion in contact with the high temperature reaction region has a higher temperature, and thus such a member may corrode.

The range of a high temperature reaction region can be represented by equation $\ln(LV) = a \ln(L/D)$ (hereinafter also called equation (1)), where D is the diameter (mm) of an outlet 23a, LV is the blowing linear velocity (m/s) of fluorine gas as converted at a temperature of 0° C. and a pressure of 0 MPaG, and L is the length (mm) (the length in a fluorine gas ejecting direction) of a formed high temperature reaction region. In the equation, ln is natural logarithm, and a is a constant and can be a value of 1.2 or more and 1.4 or less. From the equation, the length of an expected high temperature reaction region can be calculated, and this enables a design such that a high temperature reaction region is not in contact with a member.

The direction along the major axis of a high temperature reaction region (the axis along a fluorine gas ejecting direction) may be any direction, and fluorine gas is preferably ejected from the outlet 23a at an angle of 90° (horizontal direction) or more and 180° or less so as to stably maintain a high temperature reaction region to a maximum extent, where the vertically downward direction is 0°, and the vertically upward direction is 180°.

The reaction apparatus includes a temperature measurement device (not illustrated) for measuring the temperature of a raw material liquid 1 and includes the circulator having the heat exchanger 19, and thus the reaction can be performed while a raw material liquid 1 is cooled to control the temperature of the raw material liquid 1. Accordingly, an abnormal temperature increase of a reaction field or damage on the reaction apparatus can be suppressed. The temperature of a raw material liquid 1 can be set at 0° C. or more and 200° C. or less, for example. The reaction pressure can be set, for example, at 0.01 MPaA (absolute pressure) or more and 1.0 MPaA (absolute pressure) or less and preferably normal pressure or more and 0.9 MPaG or less.

The reaction apparatus may include a device for measuring the liquid level of a raw material liquid 1. For example, a device of measuring the liquid level from the differential pressure between a liquid phase and a gas phase in the reaction container 11 or a device of measuring the liquid level by using a float can be used.

As the synthesis reaction of tetrafluoromethane proceeds, the liquid level of a raw material liquid 1 decreases. If the liquid level can be measured, a raw material liquid 1 can be supplied into the reaction container 11 while the liquid level is continuously or intermittently monitored, and thus tetrafluoromethane can be continuously synthesized The concentration of fluorine gas used in the reaction is not limited to particular values, and 100% fluorine gas may be used, or a fluorine gas diluted with an inert gas such as nitrogen gas and argon may be used.

To uniformly react the blown fluorine gas with a raw material liquid 1, the reaction container 11 may include a stirrer having stirring blades for stirring the raw material liquid 1.

EXAMPLES

The present invention will next be described more specifically with reference to examples and comparative examples.

Example 1

Tetrafluoromethane was synthesized by using a reaction apparatus substantially the same as the reaction apparatus in FIG. 1 except that a heat exchanger 19, a circulation pipe 28, and a liquid circulating pump 15 were not included. In an SUS reaction container having a capacity of 1 L, 600 mL (1,030 g) of perfluoro-n-octane having a boiling point of 103° C. at normal pressure was placed, and to an outlet having a diameter of 1 mm and provided at an end of the fluorine gas pipe, an aggregated polyethylene (a low-density polyethylene (LDPE) manufactured by Aldrich) was attached as a reaction inducer. The content of the polyethylene used was 0.5% by mass where the total content of the perfluoro-n-octane and the polyethylene was 100% by mass.

From the fluorine gas outlet provided at an end of the fluorine gas pipe, fluorine gas was introduced to perfluoro-n-octane as a raw material liquid. The blowing flow rate of fluorine gas was set at 400 mL/min as converted at a temperature of 0° C. and a pressure of 0 MPaG, and the blowing linear velocity was set at 2.1 m/s.

When the introduction of fluorine gas was started, the temperature of the outlet increased to 200° C. The reaction continued while the reaction container was cooled from the outside, and the reaction was performed while the temperature of the raw material liquid was maintained at 25° C., and the reaction pressure was maintained at normal pressure. As a result, the reaction was performed while the temperature of the outlet was maintained at 200° C.

The produced gas was sampled and analyzed, and consequently the produced gas contained 95% by volume tetrafluoromethane and 5% by volume hexafluoroethane. Of the reacted perfluoro-n-octane, 95% by mole was converted into tetrafluoromethane, and the yield of tetrafluoromethane was 95%. No unreacted fluorine gas was detected in the produced gas.

After the completion of the reaction, the outlet of the fluorine gas pipe was observed. No corrosion or the like was observed, and the outlet maintained the same shape as the shape before the reaction. In addition, no corrosion or the like was observed on the thermocouple for measuring the temperature of the outlet or the raw material liquid and on the reaction container.

Example 2

Reaction was performed in the same manner as in Example 1 except that a reaction apparatus included a stirrer having three inclined paddle blades, and a powdery polystyrene was dispersed as a reaction inducer in the raw material liquid. The polystyrene was manufactured by Aldrich and was a powder having an average particle diameter of 250 μm. The content of the polystyrene was 0.5% by where the total content of the perfluoro-n-octane and the polystyrene was 100% by mass. To disperse the powdery polystyrene, the raw material liquid was stirred by using the stirrer at a rotation speed of 400 min$^{-1}$.

When the introduction of fluorine gas was started, the temperature of the outlet increased to 200° C. The reaction was performed while the reaction container was cooled from the outside, and the reaction was performed while the temperature of the raw material liquid was maintained at 25° C., and the reaction pressure was maintained at normal pressure. As a result, the reaction was performed while the temperature of the outlet was maintained at 200° C.

The produced gas was sampled and analyzed, and consequently the produced gas contained 95% by volume tetrafluoromethane and 5% by volume hexafluoroethane. Of the reacted perfluoro-n-octane, 95% by mole was converted into tetrafluoromethane, and the yield of tetrafluoromethane was 95%. No unreacted fluorine gas was detected in the produced gas.

After the completion of the reaction, the outlet of the fluorine gas pipe was observed. No corrosion or the like was observed, and the outlet maintained the same shape as the shape before the reaction. In addition, no corrosion or the like was observed on the thermocouple for measuring the temperature of the outlet or the raw material liquid and on the reaction container.

Comparative Example 1

Reaction was performed in the same manner as in Example 1 except that no reaction inducer (polyethylene) was used, and perfluoro-n-octane was used as a raw material liquid. Although introduction of fluorine gas was continued for 5 hours, the temperature of the outlet was not changed, and the entire amount of the introduced fluorine gas was discharged in an unreacted state from the gas discharge pipe for discharging a gas phase in the reaction container to the outside. In the discharged fluorine gas, no tetrafluoromethane was detected, and the yield of tetrafluoromethane was 0%.

Example 3

Tetrafluoromethane was synthesized by using a reaction apparatus substantially the same as the reaction apparatus illustrated in FIG. 1. In an SUS reaction container having a capacity of 4 m$^3$, 4,700 kg (2.8 m$^3$) of hexafluorotetrachlorobutane was placed, and 33.1 kg of an aggregated polystyrene in total was attached as a reaction inducer to seven outlets each having a diameter of 5 mm and provided at an end of the fluorine gas pipe. The content of the hexafluorotetrachlorobutane used was 99.3% by mass and the content of the polystyrene used was 0.7% by mass where the total content of the hexafluorotetrachlorobutane and the polystyrene was 100% by mass.

From the outlets of a fluorine gas pipe, fluorine gas was introduced to the raw material liquid, and reaction was performed while the temperature of the raw material liquid was controlled at 60° C., and the reaction pressure was controlled at 0.2 MPaG. As the fluorine gas pipe, a ring sparger having seven outlets with a diameter of 5 mm was used. The blowing flow rate of fluorine gas ejected from each outlet was set at 277 mL/min as converted at a temperature of 0° C. and a pressure of 0 MPaG, and the blowing linear velocity was set at 45 m/s.

Near one outlet of the seven outlets, a thermocouple was installed, and the reaction was performed while the temperature of the outlet was measured. When the value a in equation (1) is 1.27, a high temperature reaction region having a length of 100 mm is expected to be formed for each outlet. Hence, in the range where the high temperature reaction regions were to be formed, any member of the reaction apparatus was not placed except the one thermocouple.

When the introduction of fluorine gas was started, the temperature of the outlet increased to 190° C. The reaction was performed while the raw material liquid was circulated and was cooled by the heat exchanger, and the reaction was performed while the temperature of the raw material liquid was maintained at 60° C., and the reaction pressure was maintained at normal pressure. As a result, the reaction was performed while the temperature of the outlet was maintained at 190° C.

When the introduction of fluorine gas was started, the liquid level of the raw material liquid was started to decrease, and concurrently tetrafluoromethane was formed. Of the supplied fluorine gas, 84% by mole was consumed in forming tetrafluoromethane, and the remaining (16% by mole) fluorine gas was consumed in forming fluorochlorinated carbon compounds having two or more carbon atoms. In the reaction, the reaction rate of hexafluorotetrachlorobutane was 100%, and thus the yield of the tetrafluoromethane was 84% on the basis of hexafluorotetrachlorobutane.

The reaction was performed while hexafluorotetrachlorobutane was supplied to the reaction container to maintain the liquid level of the raw material liquid. As a result, the reaction continued stably until the supply of fluorine gas was stopped.

After the completion of the reaction, the outlet of the fluorine gas pipe was observed. No corrosion or the like was observed, and the outlet maintained the same shape as the shape before the reaction. In addition, no corrosion or the like was observed on the chamber wall of the reaction container and the like.

Comparative Example 2

Reaction was performed in the same manner as in Example 2 except that no reaction inducer (polystyrene) was used, and perfluoro-n-octane was used as a raw material liquid. As a result, the temperature of the outlet was not changed, and the entire amount of the introduced fluorine gas was discharged in an unreacted state from the gas discharge pipe for discharging a gas phase in the reaction container to the outside. In the discharged fluorine gas, no tetrafluoromethane was detected, and the yield of tetrafluoromethane was 0%.

Example 4

Tetrafluoromethane was synthesized by using a reaction apparatus substantially the same as the reaction apparatus illustrated in FIG. 1 except that a heat exchanger 19, a circulation pipe 28, and a liquid circulating pump 15 were not included. In a colorless, transparent pressure-resistant glass reaction container having a capacity of 1 L, 600 mL (1,000 g) of hexafluorotetrachlorobutane was placed, and to an outlet having a diameter of 1 mm and provided at an end of the fluorine gas pipe, an aggregated polystyrene (a polystyrene manufactured by Aldrich, a balled film having a film thickness of 0.05 mm) was attached as a reaction inducer. The content of the hexafluorotetrachlorobutane used was 99.7% by mass and the content of the polystyrene used was 0.3% by mass where the total content of the hexafluorotetrachlorobutane and the polystyrene was 100% by mass.

From the outlet of the fluorine gas pipe, fluorine gas was introduced to the raw material liquid. The blowing flow rate of fluorine gas was set at 400 mL/min as converted at a temperature of 0° C. and a pressure of 0 MPaG, and the blowing linear velocity was set at 2.1 m/s. When the introduction of fluorine gas was started, the formation of a high temperature reaction region was visually observed on the outlet, and the temperature of the outlet increased to 200° C. The reaction was performed while the reaction container was cooled from the outside, and the reaction was performed while the temperature of the raw material liquid was maintained at 25° C., and the reaction pressure was maintained at normal pressure.

The transparent raw material liquid was turned into black due to soot generated by the reaction, but 81% by mole of the introduced fluorine gas was consumed by the reaction of forming a gas, and 85% by volume of the formed gas was tetrafluoromethane. The yield of tetrafluoromethane was 75% on the basis of hexafluorotetrachlorobutane. Unreacted fluorine gas was not detected.

Example 5

Tetrafluoromethane was synthesized by using a reaction apparatus substantially the same as the reaction apparatus in FIG. 1 except that a heat exchanger 19, a circulation pipe 28, and a liquid circulating pump 15 were not included but a stirrer having six flat turbine blades was included. The fluorine gas pipe has a structure enabling concurrent introduction of nitrogen gas in addition to fluorine gas, and a fluorine gas diluted with nitrogen gas can be introduced to a raw material liquid. In addition, the diameter of a fluorine gas outlet provided at an end of the fluorine gas pipe is variable.

The temperature of the fluorine gas outlet can be measured by a thermocouple. If a combustion reaction by fluorine gas is caused near the outlet, the temperature of the outlet becomes higher than the temperature of a raw material liquid, and thus the occurrence of a combustion reaction by fluorine gas can be detected. On a gas discharge pipe of the reaction container, a regulator valve is installed to change the reaction pressure in the reaction container.

In an SUS reaction container having a capacity of 1 L, 600 mL (1,000 g) of hexafluorotetrachlorobutane was placed, and to an outlet of the fluorine gas pipe, an aggregated polystyrene (a polystyrene manufactured by Aldrich, a balled film having a film thickness of 0.05 mm) was attached as a reaction inducer. The content of the hexafluorotetrachlorobutane used was 99.7% by mass and the content of the polystyrene used was 0.3% by mass where the total content of the hexafluorotetrachlorobutane and the polystyrene was 100% by mass.

The diameter of the fluorine gas outlet was set at 2.2 mm, and through the outlet, a fluorine gas diluted with nitrogen gas to have a concentration of 40% by volume was introduced to the raw material liquid. The blowing flow rate of the fluorine gas diluted with nitrogen gas was set at 400 mL/min as converted at a temperature of 0° C. and a pressure of 0 MPaG, and the blowing linear velocity was set at 0.4 m/s.

When the introduction of the fluorine gas diluted with nitrogen gas was started, the temperature of the outlet increased to 150° C. The reaction was performed while the raw material liquid was stirred with the stirrer at a rotation speed of 360 min$^{-1}$, and the reaction container was cooled or heated from the outside, and the reaction was performed while the temperature of the raw material liquid was maintained at 70° C., and the reaction pressure was maintained at 0.35 MPaG.

When the introduction of fluorine gas was started, tetrafluoromethane was formed. Of the supplied fluorine gas, 90% by mole or more was consumed in forming tetrafluoromethane. The yield of tetrafluoromethane was 90% on the basis of hexafluorotetrachlorobutane.

After the completion of the reaction, the outlet of the fluorine gas pipe was observed. No corrosion or the like was observed, and the outlet maintained the same shape as the shape before the reaction.

Comparative Example 3

In an SUS reaction container having a capacity of 500 mL, 500 mL of activated carbon as a solid reaction raw material (carbon source) was placed, and the lower part of the reaction container was heated to 450° C. The upper part of the reaction container was open to the atmosphere. An fluorine gas pipe made from SUS and having an outer diameter of 3 mm and an inner diameter of 1 mm was placed such that the distance between the fluorine gas outlet and the activated carbon was 5 mm, and fluorine gas having a concentration of 100% by volume was blown from the outlet to the activated carbon. The blowing flow rate of fluorine gas was set at 400 mL/min as converted at a temperature of 0° C. and a pressure of 0 MPaG, and the blowing linear velocity was set at 2.1 m/s.

After a while from the start of blowing of fluorine gas, fluorine gas and the activated carbon were started to be reacted with flames, and concurrently, fluorine gas and SUS were reacted to generated sparks from the outlet of the fluorine gas pipe. The fluorine gas pipe was then gradually shortened by the reaction between fluorine gas and SUS, and the fluorine gas pipe was continued to burn until the introduction of fluorine gas was stopped.

Comparative Example 4

In an SUS cylindrical reaction container, 100 mL of activated carbon was packed as a solid reaction raw material (carbon source), then the outer surface of the cylindrical reaction container was heated to 450° C. with an electric heater, and concurrently fluorine gas and nitrogen gas were introduced to the cylindrical reaction container. Fluorine gas and nitrogen gas were blown such that the concentration of fluorine gas was 10% by volume in the introduced mixed gas of fluorine gas and nitrogen gas, and the blowing flow rate of fluorine gas was set at 90 mL/min, whereas the blowing flow rate of fluorine gas was set at 10 mL/min, as converted at a temperature of 0° C. and a pressure of 0 MPaG. The blowing linear velocity was set at 0.0008 m/s.

The temperature of the activated carbon increased to 500° C. The reaction gas in the cylindrical reaction container discharged from the outlet of the cylindrical reaction container was analyzed. As a result, the concentration of tetrafluoromethane was 48% by volume, and fluorinated carbon compounds having two or more carbon atoms were detected as other gaseous components.

After the completion of the reaction, the cylindrical reaction container was cut, then the inner surface was observed, and pitting corrosion was partially observed.

REFERENCE SIGNS LIST 1 raw material liquid
11 reaction container
23 fluorine gas pipe
23a outlet

The invention claimed is:

1. A method for producing tetrafluoromethane, the method comprising:
   introducing fluorine gas to a raw material liquid containing a reaction inducer and a fluorinated hydrocarbon represented by chemical formula $C_pH_qCl_rF_s$ (in the chemical formula, p is an integer of 3 or more and 18 or less, q is an integer of 0 or more and 3 or less, r is an integer of 0 or more and 9 or less, and s is an integer of 5 or more and 30 or less) and having no carbon-carbon unsaturated bond,
   wherein the reaction inducer is a hydrocarbon polymer solid at normal temperature and pressure and is reacted with the fluorine gas to induce a reaction of forming tetrafluoromethane from the fluorinated hydrocarbon and the fluorine gas.

2. The method for producing tetrafluoromethane according to claim 1, wherein the reaction inducer is contained at a content of more than 0% by mass and not more than 1% by mass where a total content of the fluorinated hydrocarbon and the reaction inducer contained in the raw material liquid is 100% by mass.

3. The method for producing tetrafluoromethane according to claim 2, wherein the hydrocarbon polymer is at least one polymer selected from polyethylene, polypropylene, polystyrene, and paraffin.

4. The method for producing tetrafluoromethane according to claim 1, wherein the fluorinated hydrocarbon is at least one fluorine-containing substance selected from a perfluorocarbon, a fluorohydrocarbon, a chlorofluorocarbon, a chlorofluorohydrocarbon, and a chlorotrifluoroethylene polymer.

5. The method for producing tetrafluoromethane according to claim 2, wherein the fluorinated hydrocarbon is at least one fluorine-containing substance selected from a perfluorocarbon, a fluorohydrocarbon, a chlorofluorocarbon, a chlorofluorohydrocarbon, and a chlorotrifluoroethylene polymer.

6. The method for producing tetrafluoromethane according to claim 3, wherein the fluorinated hydrocarbon is at least one fluorine-containing substance selected from a perfluorocarbon, a fluorohydrocarbon, a chlorofluorocarbon, a chlorofluorohydrocarbon, and a chlorotrifluoroethylene polymer.

* * * * *